United States Patent
Mooradian et al.

(10) Patent No.: US 7,128,748 B2
(45) Date of Patent: Oct. 31, 2006

(54) CIRCULAR STAPLER BUTTRESS COMBINATION

(75) Inventors: Daniel L. Mooradian, Eagan, MN (US); B. Nicholas Oray, Woodbury, MN (US)

(73) Assignee: Synovis Life Technologies, Inc., St. Paul, MN (US)

( * ) Notice: Subject to any disclaimer, the term of this patent is extended or adjusted under 35 U.S.C. 154(b) by 434 days.

(21) Appl. No.: 10/109,595

(22) Filed: Mar. 26, 2002

(65) Prior Publication Data
US 2003/0183671 A1 Oct. 2, 2003

(51) Int. Cl.
*A61B 17/08* (2006.01)
*A61B 17/10* (2006.01)

(52) U.S. Cl. .................... 606/151; 606/153; 227/180.1

(58) Field of Classification Search ............... 606/151, 606/153, 213–215, 219, 75; 227/175.1, 180.1, 227/179.1; 623/1.13, 1.23
See application file for complete search history.

(56) References Cited

U.S. PATENT DOCUMENTS

| | | | |
|---|---|---|---|
| 3,953,566 A | 4/1976 | Gore | |
| 4,592,354 A | 6/1986 | Rothfuss | |
| 4,665,917 A | 5/1987 | Clanton et al. | |
| 5,104,025 A | 4/1992 | Main et al. | |
| 5,222,963 A | 6/1993 | Brinkerhoff et al. | |
| 5,250,058 A | 10/1993 | Miller et al. | |
| 5,263,629 A | 11/1993 | Trumbull et al. | |
| 5,346,501 A | 9/1994 | Regula et al. | |
| 5,468,253 A | 11/1995 | Bezwada et al. | |
| 5,503,638 A | 4/1996 | Cooper et al. ................. 623/11 |
| 5,549,628 A | 8/1996 | Cooper et al. ............... 606/220 |
| 5,575,803 A | 11/1996 | Cooper et al. ............... 606/151 |
| 5,713,920 A | 2/1998 | Bezwada et al. | |
| 5,752,965 A | 5/1998 | Francis et al. ............... 606/151 |
| 5,782,914 A | 7/1998 | Schankereli .................. 623/11 |
| 5,908,427 A | 6/1999 | McKean et al. | |
| 5,964,774 A | 10/1999 | McKean et al. | |
| 6,099,551 A | 8/2000 | Gabbay ....................... 606/219 |
| 6,165,217 A | 12/2000 | Hayes | |
| 6,273,897 B1 | 8/2001 | Dalessandro et al. ........ 606/139 |
| 6,309,423 B1 | 10/2001 | Hayes | |

(Continued)

FOREIGN PATENT DOCUMENTS

WO    WO 01/54594    8/2001

(Continued)

OTHER PUBLICATIONS

Feil/Lippert/Lozac'h/Palazzini (eds.), "History of Mechanical Stapling", *Atlas of Surgical Stapling*, pp. 3-7; 19-21.

(Continued)

*Primary Examiner*—Julian W. Woo
(74) *Attorney, Agent, or Firm*—Fredrikson & Byron, P.A.

(57) ABSTRACT

A combination medical device comprising a circular stapler instrument and one or more portions of preformed buttress material adapted to be stably positioned upon the staple cartridge and/or anvil components of the stapler prior or at the time of use. Positioned buttress material(s) are delivered to a tissue site where the circular stapler is actuated to connect previously severed tissue portions. The buttress material is retained and provides an improved seal between the joined tissue sections. The buttress material is made up of two regions, one of which serves primarily to secure the buttress material to the stapler prior to actuation, and one of which serves primarily to form the improved seal. The former region is severed and discarded upon activation of the circular stapler to form an anastomoses. Methods of use and preparation of the buttress material are also described.

54 Claims, 6 Drawing Sheets

U.S. PATENT DOCUMENTS

| | | |
|---|---|---|
| 6,312,474 B1 | 11/2001 | Francis et al. ............... 623/23 |
| 6,325,810 B1 | 12/2001 | Hamilton et al. |
| 6,468,313 B1 | 10/2002 | Claeson et al. .......... 623/23.72 |
| 6,503,257 B1 | 1/2003 | Grant et al. |
| 6,503,259 B1 | 1/2003 | Huxel et al. |
| 6,540,758 B1 * | 4/2003 | Raza ........................ 606/153 |
| 6,592,597 B1 | 7/2003 | Grant et al. |
| 6,638,285 B1 | 10/2003 | Gabbay |
| 6,656,193 B1 | 12/2003 | Grant et al. |
| 2003/0178465 A1 | 9/2003 | Bilotti et al. |
| 2005/0059996 A1 | 3/2005 | Bauman et al. |
| 2005/0059997 A1 | 3/2005 | Bauman et al. |

FOREIGN PATENT DOCUMENTS

| | | |
|---|---|---|
| WO | WO 03/82126 | 3/2002 |
| WO | WO 05/027983 | 3/2005 |

OTHER PUBLICATIONS

L.E. Smith, "Anastomosis with EEA stapler after colonic resection" *Dis. Colon Rectum 24*, 236 (1981).

* cited by examiner

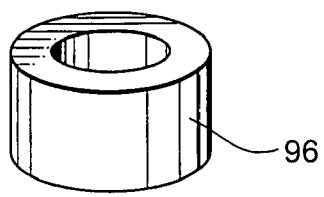
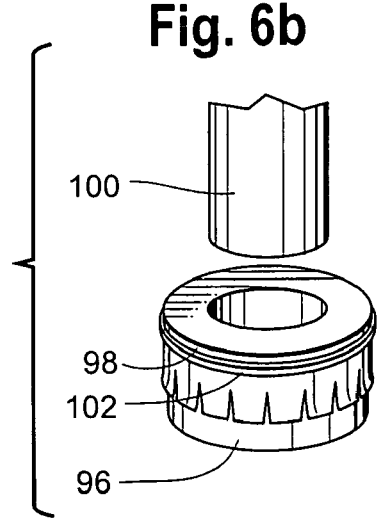
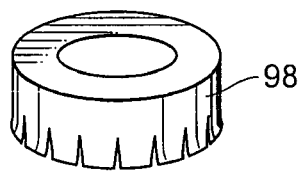
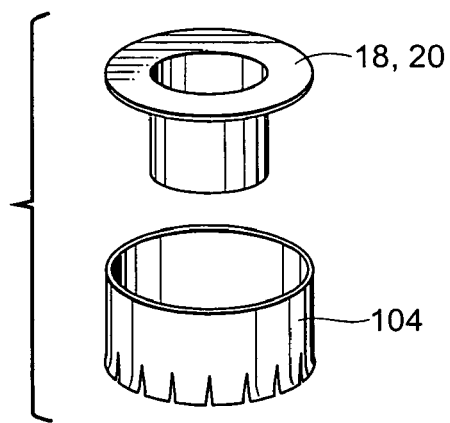

CIRCULAR STAPLER BUTTRESS COMBINATION

TECHNICAL FIELD

In one aspect, the invention relates to surgical staplers, including circular staplers. In another aspect, the invention relates to surgical stapling procedures that include the use of buttress and reinforcing materials formed of stabilized tissues and polymeric materials. In yet another aspect, the invention relates to the preparation and use of preformed heterologous tissues for implantation within the body.

BACKGROUND OF THE INVENTION

Surgical staplers have been used for over a century for providing leak-proof and hemostatic wound closures. See, for instance, "History of Mechanical Stapling", pages 3–7 in Atlas of Surgical Stapling, Feil/Lippert/Lozac'h/Palazzini (eds.). More recently, circular staplers have been developed, having particular use in gastrointestinal surgery to facilitate inverted end-to-end, end-to-side and side-to-side anastomoses. (See pages 19–21, Atlas of Surgical Stapling cited above).

Surgical stapling instruments typically have a mechanism for firing a plurality of staples from a staple holding cartridge, and an anvil disposed opposite the staple cartridge against which the staples are formed. Such instruments include, for example, linear staplers, which typically apply one or more parallel rows of staples, and circular staplers, which typically apply one or more concentric and circular rows of staples. In use, the surgeon will place tissue between the staple cartridge and anvil and, by firing the instrument, cause the staples to become clenched to the tissue.

Circular staplers are known and have been successfully used in surgical procedures for many years. Commercially available instruments include the CEEA™. circular stapler, manufactured by United States Surgical Corporation, Norwalk, Conn., and the ILS™ circular stapler, manufactured by Ethicon, Inc., Blue Ash, Ohio. These instruments are typically indicated for use in gastric and esophageal surgery wherein tubular organs are joined to other anatomical structures.

In one common procedure, known as end-to-end anastomosis, a portion of the intestinal tract is removed (i.e., due to the presence of disease such as cancer) and the remaining ends are rejoined by using a circular stapler. To join the tubular structures, one end of intestine is secured about an anvil and the other end of intestine is held in place adjacent a staple cartridge. Preferably, the anvil has a shaft that is removably connected to the instrument. Once the anvil shaft is secured to the instrument, the anvil is drawn into close approximation to the stapling cartridge. The instrument is then fired to cause the staples to pass through tissue of both organs and become formed against the anvil. During the firing step, a circular knife is advanced to cut tissue inside the staple line, thereby establishing a passage between the organs. After firing, the instrument is typically removed by withdrawing the anvil through the staple line, after which the surgeon will carefully inspect the surgical site to ensure a proper anastomosis (joining) has been achieved.

While circular staplers have been extremely helpful in a number of surgical procedures, when used alone they are prone to creating a number of complications. An early survey of stapler-related complications revealed that in the 3594 end-to-end anastomoses conducted, intraoperative complications were reported in 15.1% of patients and included anastomotic leak, tear during stapler extraction, bleeding, and other complications. L. E. Smith, "Anastomosis with EEA stapler after colonic resection" Dis. Colon Rectum 24, 236 (1981). More recent studies have indicated that postoperative leakage, which can be quite dangerous in gastrointestinal tissue, continues to be a significant problem.

On a different subject, a variety of references teach the preparation of "buttress," "pledget" or "reinforcing" materials for use in combination with conventional surgical staplers. See generally, Applicant's own U.S. Pat. Nos. 5,503,638, 5,549,628, 5,575,803, 5,752,965, 5,782,914 and 6,312,474.

By comparison, relatively few references suggest the use of buttress materials for use with circular staplers. Presumably, this is due to the problems inherent in positioning and using such materials, particularly since neither the shape of a circular stapler, or the demands of its use, are conducive to the placement or use of conventional buttress materials (e.g., pledgets). For instance, U.S. Pat. No. 6,273,897, which discloses a surgical buttress for use with linear staplers, mentions immediately before the claims that "the present invention may be similarly utilized in conjunction with other types of surgical staplers and cutters. For example, a circular stapler . . . may be suitably modified to provide buttresses on the staple cartridge and the anvil."

On a separate subject, Applicants have also previously described the preparation and use of "preformed" tissue implants. See published International Application No. WO 99/48540, the disclosure of which is incorporated herein by reference.

What is clearly needed are materials and methods for providing surgical staple lines, and particularly circular staplers, having improved properties such as staple line strength and buttress seal.

SUMMARY OF THE INVENTION

In one aspect, the present invention provides a combination medical device comprising:

(a) a circular stapler instrument, comprising a staple cartridge component and corresponding anvil component, and (b) one or more portions of buttress material adapted to be a) stably positioned upon the staple cartridge and/or anvil components of the stapler prior to, or at the time of, use, b) while in position upon the stapler component(s), to then be delivered to a tissue site in combination with the stapler components, c) upon delivery of the components and positioned material portion(s) to the tissue site, to provide a first region of buttress material as a staple line buttress seal retained between joined tissue sections upon activation of the stapler, and optionally and preferably, d) to permit the removal of one or more portions of a second region of the buttress material upon activation of a stapler knife provided by the stapler.

The buttress material is adapted to be positioned upon a respective stapler component in a manner sufficient to permit the material to be delivered with the component into the body and to a surgical anastomotic site. By virtue of its physical structure, optionally aided with ancillary materials described herein, the material retains sufficient properties, including shear resistance, to avoid being dislodged or delaminated from its position in the course of positioning.

Optionally, buttress material can include the use of one or more portions of a third region, e.g., axial and external to the second region, for instance in the form of material that extends beyond the rim of a stapler component, and is used to slip fit the material over the component. While it is generally not preferable to include third region portions that would extend beyond the tissue sections being joined (given their tendency to prompt the formation of adhesions within the tissue site), such regions can be provided in a form that permits them to be either removed or biodegraded over time, if desired.

In other aspects, the invention provides a kit comprising preformed buttress material of suitable dimensions to prepare a combination as described above, as well as a method of making and a method of using both the buttress materials themselves and the resultant combination. The buttress material can be provided in dry (e.g., dehydrated) form, or at any suitable stage of hydration. The material can also be packaged separately from the stapler components, or in a manner pre-positioned upon the components. Also optionally, positioning of the material upon a respective component can be accomplished or facilitated by the use of ancillary materials, such as gels or ties.

In a particularly preferred embodiment, the combination comprises a plurality of separate portions of buttress material, wherein each portion comprises animal tissue prepared in a manner that permits the tissue to retain a three dimensional structure corresponding to a respective stapler component. The preformed tissue portions permit the placement and retention of the portions upon respective stapler components, preferably without the need for adhesives, ties, and the like. The preformed tissue portions can be treated (e.g., chemically treated) and/or manipulated (e.g., sewn) to retain suitable three dimensional structure and topographic features (e.g., raised/indented portions, ridges) that permit them to be positioned in a secure fashion upon a respective stapler component, e.g., by press fit or friction fit onto the corresponding grooves, apertures, ridges and edges of the stapler device component. Preferred preformed materials have a "memory" that permits them to retain or assume a predetermined desired shape in the course of use, including in various stages of hydration.

The buttress material portions preferably provide two or more regions, including a first region adapted to remain in position within the body in order to serve as the staple line buttress itself, together with one or more portions of a second region adapted to assist in positioning and/or retaining the buttress material upon a stapler component. Preferably, the one or more portions of the second region are adapted to be removed from the tissue site upon activation of the stapler knife. The second region is generally concentric to, and integral with, the first region, providing a desired three dimensional and/or topographic structure adapted to position and/or retain the materials in place upon the respective stapler component. Generally, the second region is internal to the circular seam formed, and can be removed together with the severed ends of the joined tissue portions in order to provide an unobstructed lumen for the joined tissue portions.

BRIEF DESCRIPTION OF THE DRAWINGS

In the Drawings, wherein like reference numerals are utilized to designate like parts throughout the same:

FIG. 6 is a schematic view in perspective illustrating the technique for preparing a portion of buttress material.

DETAILED DESCRIPTION

Figure 1:
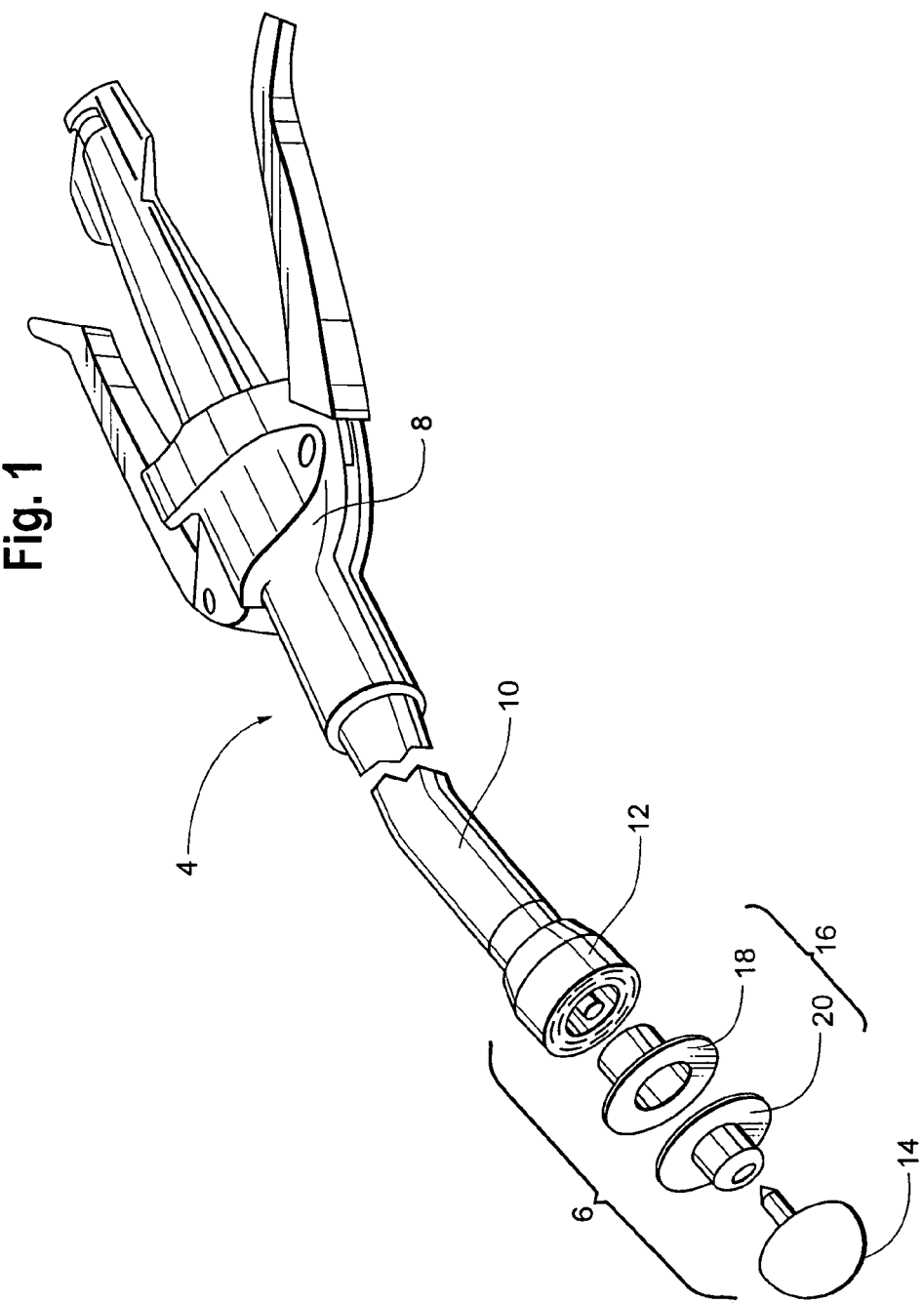
FIG. 1 is perspective view of a circular stapler, exploded at the distal end, in combination with the buttress material of the present invention.

Referring to FIG. 1, there is shown a preferred embodiment of a combination device of the present invention, including a circular surgical stapler (4) having a distal fastener head (6), a proximal handle section (8) and an elongated arm connecting the two (10). The proximal handle section allows for positioning of the staple head assembly at the surgical site and bears the controls which trigger the activation of the various components of the distal fastener head. The distal fastener head, mounted on elongated arm (10) at the distal end of the instrument, is composed of two major components, the staple cartridge component (12) and the anvil (14). Buttress material (16) is placed between the staple cartridge component (12) and the anvil (14) and preferably includes two components, the staple cartridge buttress (18) and the anvil buttress (20) which are secured to the staple cartridge and anvil components, respectively.

Figure 2:
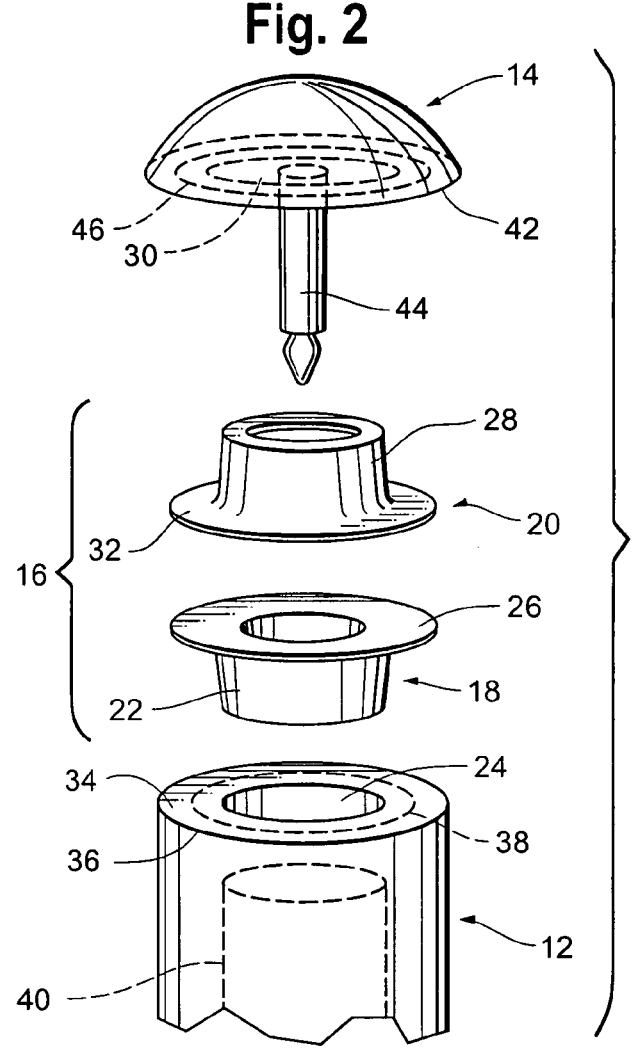
FIG. 2 is an exploded view in perspective of a circular stapler cartridge and anvil in combination with the buttress material of the present invention.

Referring to FIG. 2, the combination device of FIG. 1 is shown in more detail by focusing on the distal fastener head (6). As just described, the fastener head has two major components; the staple cartridge component (12) and a corresponding anvil component (14). Also shown is buttress material (16) adapted for use with the circular surgical stapler (4), the buttress including a staple cartridge buttress (18) adapted to be positioned upon the staple cartridge component (12) and an anvil buttress (20) adapted to be positioned upon the anvil component (14).

Connecting the staple cartridge component to the anvil component is the anvil shaft (44). The anvil shaft extends proximally and substantially perpendicular from a plane defined by the staple forming surface of anvil. The anvil shaft is longitudinally movable between a first, extended position and a second, retracted position. In the preferred embodiment, the anvil shaft can be readily detached from the staple cartridge component to allow for easy placement of the buttress component(s).

The staple cartridge buttress (18) is shown having a raised central region (22) that is dimensioned and adapted to be positioned into a recessed aperture (24) within the cartridge component (12), as well as a circumferential flat, disc-like portion (26) adapted to be positioned upon the open face (34) of the staple cartridge component (12), and to ultimately be positioned between the abutted tissue sections (and adjacent to the anvil buttress disc-like portion (32)) in order to serve as a staple line buttress.

The anvil buttress (20) is also shown having a raised central region (28) that is dimensioned and adapted to be positioned into a recessed aperture (30) within the anvil component (14), as well as a circumferential flat, disc-like portion (32) adapted to be positioned upon the open face (42) of the anvil component (14), and to ultimately be positioned between the abutted tissue sections (and adjacent to the staple cartridge buttress disc-like portion (26)) in order to serve as a staple line buttress.

In a preferred embodiment, the invention provides a surgical stapler combination for joining first and second abutting sections of tissue in order to form a circumferential seam between them. As shown in FIG. 2, the distal fastener head (6) includes a generally cylindrical staple cartridge component (12) comprising a circular face (34) having an outer edge (36), the face and edge being adapted to retain and position a terminal section of the first tissue portion. The stapler also includes a plurality of staples (38) positioned within the face and adapted to be delivered through the positioned tissue upon actuation of the stapler, as well as a generally central aperture (24), and a recessed annular scalpel blade (40) positioned within the central aperture and adapted to be delivered from the cartridge in order to sever an internal circumferential ring of tissue and buttress material.

As shown, the stapler also includes an anvil component (14), mateable with the staple cartridge component (12), and adapted to retain and position a terminal section of the second tissue portion in apposition to the positioned first tissue in the course of a surgical stapling procedure. A typical anvil component (14) has a rounded, conical shape to allow it to pass through tissue more readily. A circular face (42) forms the bottom of the conical shape and is adapted to be positioned and secured to the corresponding circular face of the staple cartridge component. The circular face bears an array of staple-forming grooves (46) adapted to clinch staples delivered through the tissue portions upon actuation of the circular stapler. Finally, the anvil component as shown includes an annular recessed aperture (30) between the conical portion and the circular face, adapted to permit the annular scalpel (40) to fully traverse, and thereby sever, tissue retained between the cartridge and anvil.

With respect to the stapler shown in these Figures, corresponding preformed buttress materials are dimensioned and adapted to be positioned over the circular face of a corresponding stapler component. The buttress materials comprise a generally planar circumferential exterior region (26 and 32) adapted to generally cover the circular face, and in turn, to be positioned between the abutting sections of tissue in order to form a seal therebetween. The buttress materials can be continuous or discontinuous (e.g., as in the form a split washer that would permit them to be slid into position around an anvil stem already positioned within a stapler component.

Figure 3:
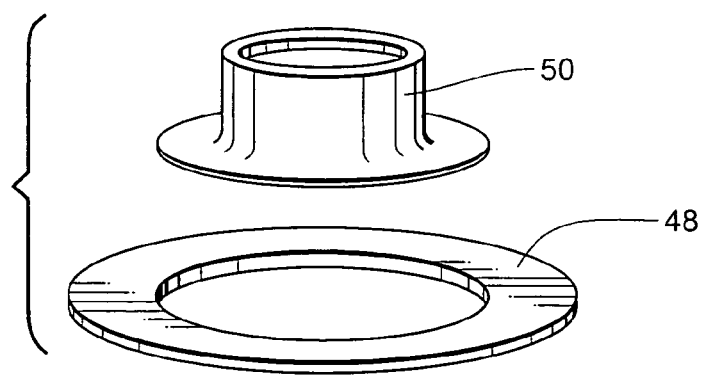
FIG. 3 is a view in perspective of buttress material in which the first and second regions are shown after being severed by a circular knife blade.
Figure 4A:
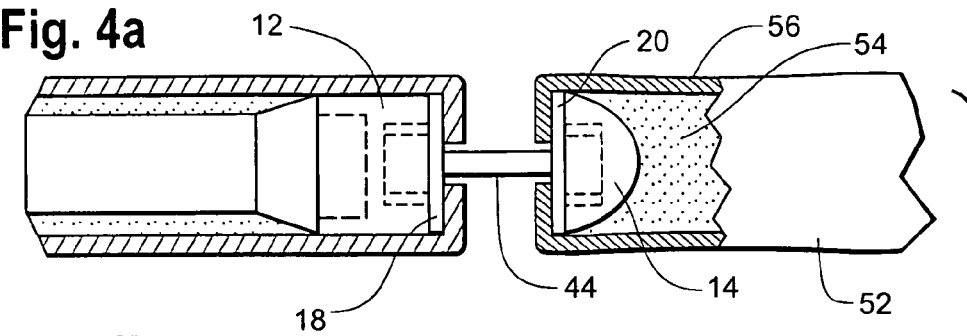
FIG. 4 is a schematic view illustrating the technique for stapling abutted tubular tissue sections using the buttress material of the present invention to form an anastomoses.
Figure 4B:
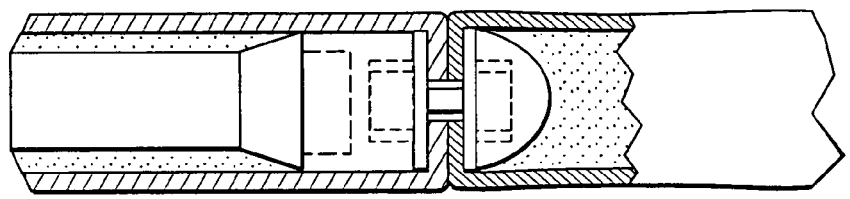
Figure 4C:
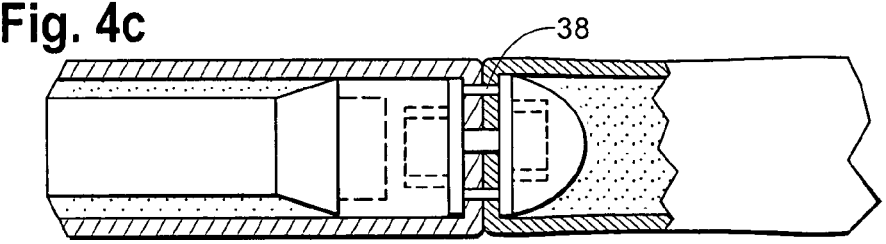
Figure 4D:
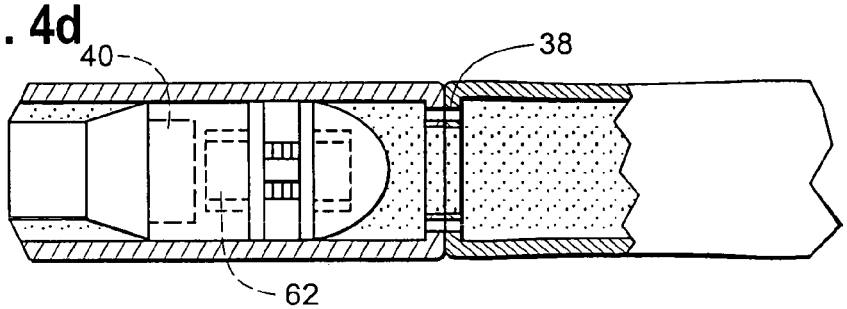

The buttress materials also provide a preformed, nonplanar interior circumferential regions (22 and 28) adapted to stably and releaseably position the material upon the face and to thereafter be severed from the buttress device upon delivery of the annular scalpel. FIG. 3 shows the two basic regions of the buttress material(s) following actuation of the stapler (including scalpel). These include a reinforcing region (48) and the discarded region (50). These are also referred to in this application as the first and second regions of a buttress, respectively. In a preferred embodiment, the system includes a plurality of preformed buttress materials, including materials adapted to be positioned on the anvil and cartridge portions.

In another aspect, the invention provides a kit for preparing a combination as described herein, as well as a buttress material, per se, adapted for such use, a method of preparing such a buttress material, and a method of performing a surgical stapling procedure using such a material and combination.

The combination of this invention can include any suitable surgical instrument for applying a circular array of fasteners, e.g., staples. Examples of suitable instruments are found, for instance, in U.S. Pat. Nos. 5,411,508, 5,558,579, and 6,102,271, the disclosures of which are incorporated herein by reference. See FIG. 1. Such instruments typically include a proximal handle section (8) and a distal fastener head (6) connected by an elongated arm (10). Throughout this description, the term "proximal" refers to the end of the apparatus closest to the operator, while the term "distal" refers to the end furthest from the operator. The handle section (8) includes various controls and levers for the operation of the instrument.

FIG. 4 shows a cross-section view of the overall process of creating a reinforced stapled connection for tubular tissue in four steps, from top to bottom, using a preferred embodiment of this invention. In the first step, two ends of tubular tissue (52) are positioned over the ends of the staple cartridge component and the anvil component respectively. The cross section of the tubular tissue wall (56) as well as the interior surface of the tubular tissue (54) are shown. The tubular tissue is typically sutured to hold it in place over the stapler components. The staple cartridge component (12) and the anvil component (14) are connected by means of the anvil shaft (44). The staple cartridge buttress (18) and the anvil buttress (20) can be seen positioned over and within their respective stapler components. Once the tubular tissue has been properly positioned, the anvil component is moved from the open position spaced away from the staple cartridge component to the closed position, in which the two components are adjacent with tissue and buttress materials sandwiched between them. This is shown in the second step of the procedure.

In the third step, firing of the instrument is accomplished by squeezing fastener firing levers present on the proximal handle section (8), as is known in the art, causing staples (38) to be ejected through tissue (56) and buttress material (18 & 20), and into contact with the corresponding anvil component (14). Upon completion of the firing stroke, staples (38) are fully formed against grooves (46) present in the anvil component. Simultaneously, or thereafter, the distal end of an annular scalpel (40) is extended through the sandwiched tissue and buttress material, until it bottoms out in a recessed annular ring within the anvil, thereby severing an inner ring of the sandwiched tissue/buttress material. The annular scalpel (40), grooves (46) and aperture (24) are shown in FIG. 2. The severed material (62) is captured within the aperture (24) of the staple cartridge component (12) and removed along with the distal fastener head, as shown in the last step of FIG. 4. Once the surgical procedure has been successfully completed, a clean cut line and an annular array of staples as well as at least one piece of buttress material holding the two previously un-joined tissue (e.g., colon) portions together remain, forming a secured and sealed anastomoses.

A buttress material of this invention can be positioned over the shaft prior to or following assembly of the anvil and staple components. Apart from positioning of the buttress material, the overall operation of fastening device is well known in the art and described in several patents, such as commonly assigned U.S. Pat. Nos. 4,576,167, 5,005,749, and 5,119,983. Except where noted otherwise, the materials utilized in the components of the surgical instrument generally include such materials as polycarbonate for housing sections and related components, and stainless steel for the anvil assembly and components which transmit forces. However, equivalent alternative materials will readily come to the mind of those skilled in the art.

It will be understood that various modifications may be made to the embodiments disclosed herein. For example, the use of buttress material on a circular stapler with a pivoting fastener head instead of a rigidly attached fastener head would be well within the invention disclosed in the present application.

Circular stapler buttress material is composed of biomaterial which is typically bovine pericardium sheet fixed onto a preformed shape using a tanning solution. The actual buttress portions used are defined by the shapes they are adapted to be positioned upon, which for a circular stapler are typically the staple cartridge and anvil components. The cartridge buttress includes a biomaterial preformed by fixing upon a template and trimming to form a disc with a central cylindrical depression with a hole at its base, which snugly fits on the staple-firing end of the staple cartridge. The anvil buttress includes a biomaterial preformed by fixing upon a template and trimming to form a ring-shaped disk with an incurvate central lip which fits snugly on the anvil-plate end of the anvil.

In accordance with the present invention, it has been discovered that certain natural animal tissues, properly preserved and processed, present superior properties for preformed buttress materials. In particular, it has been found that if the buttress materials are pre-formed in a shape corresponding to the shape of respective stapler components, and the tissue processed or cross-linked, a superior buttress is produced which facilitates the stapling procedure. In particular, bovine pericardial tissue has been used quite successfully. The processed buttress materials of the invention are sterile and readily situated and attached in place. They can be produced in all convenient sizes required.

In the process of the present invention the stapler buttress materials are formed from pre-soaked or dehydrated animal tissue using shaping forms of desired configurations and sizes. The shaping forms are covered with the buttress material which is secured in place in a manner that provides both a generally planar portion adapted to be positioned on either the cartridge or anvil face, respectively, and an interior non-planar portion adapted to be positioned within the annular aperture of such components. Either prototype stapler devices or tailor-made forms (e.g., mandrels) designed to mimic the size and configuration of the particular stapler can be used as shaping forms It will be appreciated that a preferred process for manufacturing buttress materials in the preformed, cross-linked state in accordance with the process of the present invention results in a superior and more successful material. A flow chart describing the process for manufacturing circular stapler buttresses using pericardium in accordance with the invention is shown in FIG. 5.

In accordance with the invention, it has been found that certain natural animal tissues, properly preserved and processed, present superior properties when it comes to buttress materials, particularly if manufactured in a preformed shape. In particular, bovine pericardial tissue has been used quite successfully. It will be recognized, however, that while the processes and products are described herein with particularity to the use of bovine pericardial tissue, that is intended by way of example and not limitation inasmuch as it is believed that other suitable materials can be similarly processed.

In accordance with the manufacture of the buttress materials of the invention, it is important to obtain high quality starting material. The starting material is obtained from slaughtered animals and it is necessary to preserve the condition of the harvested animal tissue. As shown at (70) in FIG. 5, the preferred starting material is raw bovine pericardial tissue. This tissue must meet certain minimum standards and is generally harvested from United States Department of Agriculture (USDA) inspected cattle that are at least one year old, which have been processed by selected slaughterhouses. The harvesting should occur within two hours of slaughter and the harvested tissue must be of a minimum size in order to be useful for processing into the materials of the invention. The harvested sacs are placed in ice water immediately after collection and the water/saline solution is frequently changed to remove residual blood. The tissue is thereafter packaged in containers which maintain a temperature in the range of 32°–55° F. (2–5° C.) and shipped to arrive for processing, preferably within 72 hours after collection.

Figure 5:
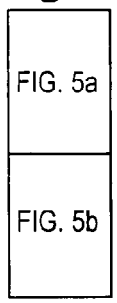
FIG. 5 is a block diagram illustrating a process for the manufacture of one type of buttress material according to the invention.
Figure 5A:
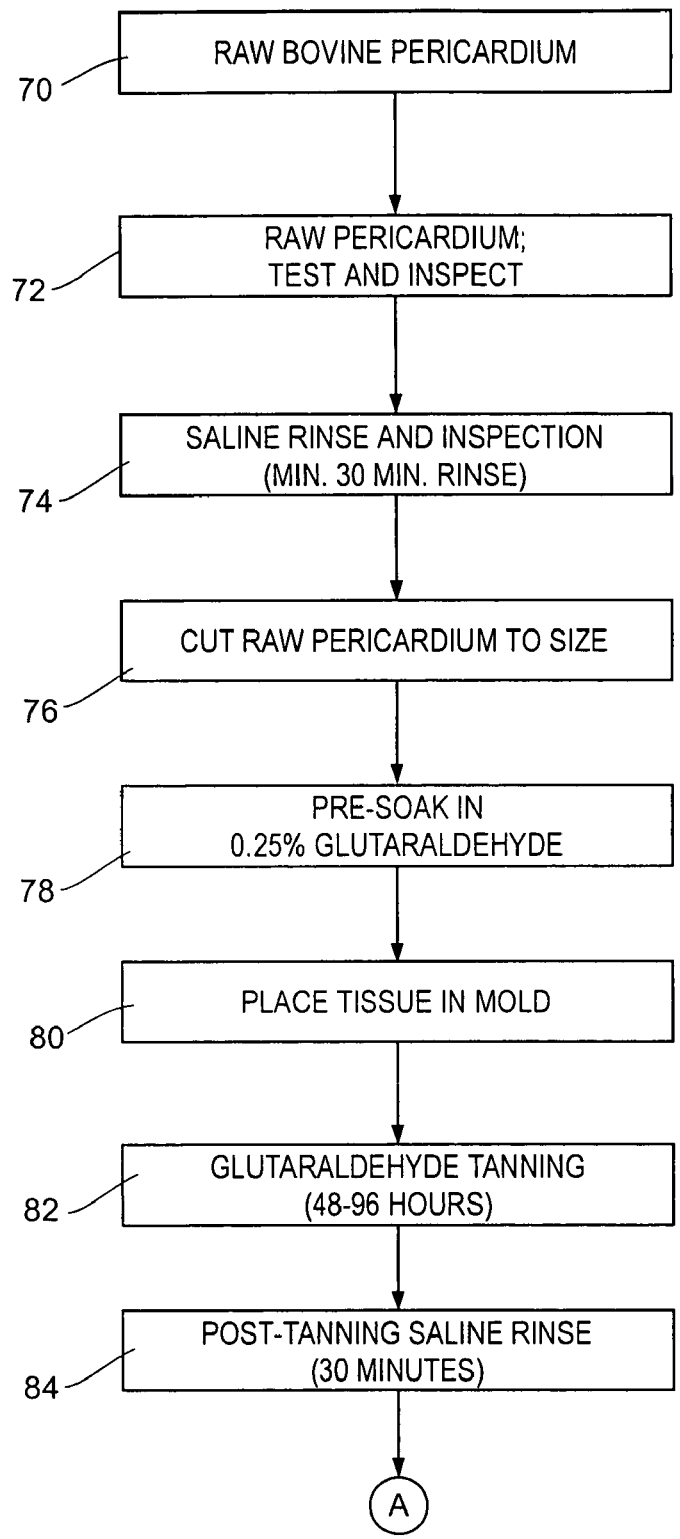
Figure 5B:
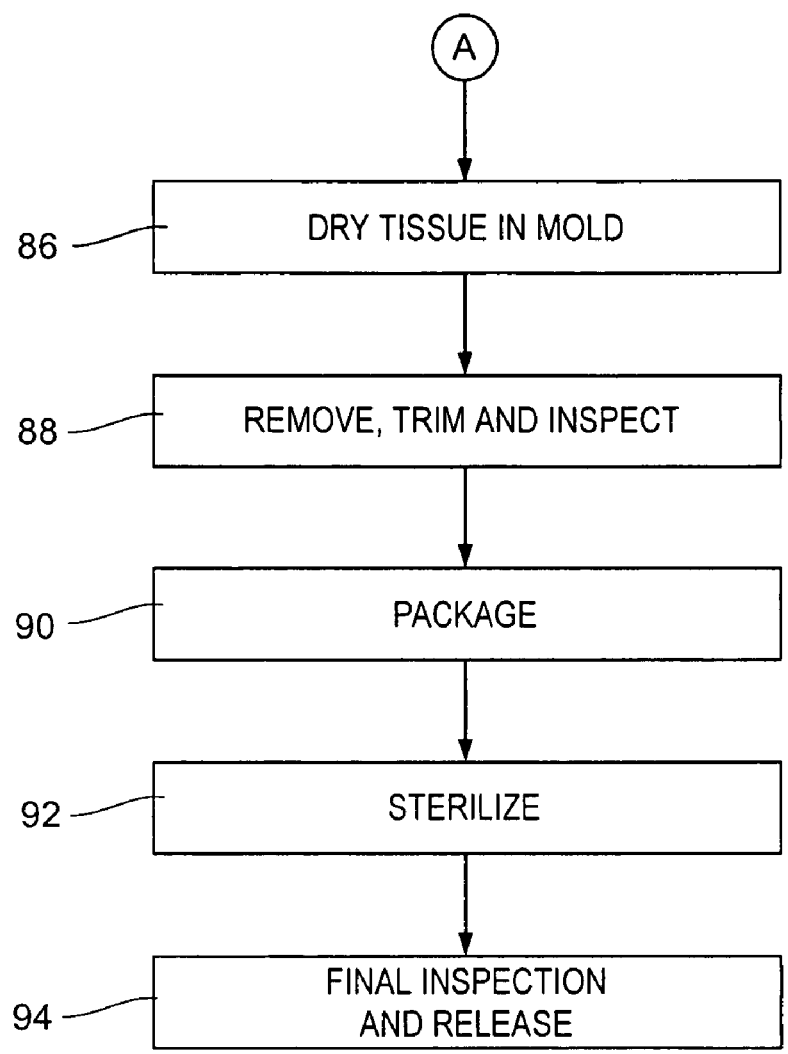

Incoming raw pericardium is initially tested and inspected (72) as shown in FIG. 5 and in accordance with a raw pericardium testing and inspection procedure that includes inspection of the material in a controlled environment for size, discoloration, environmental debris or parasites, cuts or tears (that would not afford a minimum area for use) and thickened, rough fatty or fibrous tissue. Certificates of origin and other documents are verified. The tissue is then ready for further processing.

Pericardial tissue is then subjected to a plurality of saline rinses at (74) utilizing isotonic saline. The rinses are performed in order to leach away any residual blood, and the minimum soaking time for each rinse should be approximately 30 minutes. In the case of frozen tissue, the series of cold isotonic saline rinses normally includes 2–5 rinses. If fresh tissue is used, usually 1–3 isotonic saline rinses suffice. More rinses may be used, in either case, if necessary, to remove all of the blood.

At this point in the process, a quality assurance or quality control bioburden test is performed on samples of the material to assure that the maximum bioburden is not exceeded by the material. Typically, the bioburden needs to be less than $1.0 \times 10^8$ CFU/gram of sac tissue. This is based on a randomly selected sample of approximately 10 grams representing material from each control number batch. These tests are conducted in a well-known manner. Once the quality of the material has been assured, step (76) is conducted wherein the material is cut to the appropriate size (eg. 8 cm×8 cm) for shaping into buttress material. The material is die cut using a mounted knife edge of the appropriate dimensions.

In the pre-soak (78), the cut, raw, isotonic saline-rinsed bovine pericardial tissue is transferred to trays containing approximately 0.25% glutaraldehyde solution for a minimum of 5 minutes but no longer than about 15 minutes prior to covering. After 5 minutes and before 15 minutes in the approximate 0.25% glutaraldehyde solution, the tissue, which has a shiny, visceral or inside surface and a dull, parietal or outside surface, is removed and placed on a cutting board where it is again inspected for holes, thick or thin areas, or peeling or freezer burned areas. Any extraneous tissue is cleared away from both sides of the pericardial tissue at this time.

Pre-forming of the material is now undertaken (80). In this part of the process, bovine pericardial tissue is covered around a suitable shaped device for the purpose of shaping the tissue prior to further processing. This is illustrated in detail in FIG. 6. For example, a prototype was made was made using a medium density foam with an outer diameter of 24 mm and an inner diameter of 18 mm as the shaping device, as illustrated in step 1 of FIG. 6 (96). The dimensions of the material should approximate those of the stapler components for which the buttress material is intended.

A single sheet of cut pericardial material (98) should then be placed evenly over the shaping device (96), as shown in the second step of FIG. 6. A short segment of plastic tubing (100) (e.g., with an outer diameter of 17 mm) is then used to force the pericardium into the foam template to a depth of approximately 1 cm. A rubber band (102) is then placed to hold the edges of the pericardium against the outer surface of the foam template. Wrinkles in the buttress surface are removed by manual smoothing, taking care not to stretch the tissue or force the plastic tubing (100) out of the central hole.

The tissue-covered form is placed in a lyophilizer vessel filled with enough 0.25% gluteraldehyde solution to cover the fixtures. A vacuum is pulled briefly to evacuate the air from the fixture and to replace it with 0.25% gluteraldehyde solution. The foam has been suitably affected by the vacuum when the tissue covered foam assemblies sink in the solution of 0.25% gluteraldehyde.

For gluteraldehyde tanning (82), the tissue covered form is placed in a fixation tank containing 0.25% gluteraldehyde solution. After al tissue-covered forms are placed in the tank, additional 0.25% gluteraldehyde is added to insure that all covered forms are fully immersed. The covered forms are allowed to remain in the gluteraldehyde solution at room temperature for a minimum of 48 hours and a maximum of 96 hours prior to removal.

The tissue-covered form is then placed in a lyophilizer vessel filled with enough deiononized (DI) water to cover the fixtures (84). A vacuum is pulled briefly to force DI water into the foam. The fixture containing tissue is then transferred back to the fixation vessels containing DI water for 15–120 minutes.

If used dry, the now chemically fixed tissue is then vacuum dried while on the form and the tissue is subsequently removed from the form (86). The dried, separated pericardium (98) is shown in FIG. 6. The tissue is then placed face down, support ring up, and circularly cut evenly about the support ring to the desired diameter (88). The diameter is dictated by outer diameter of desired intraluminal stapler. This results in a formed portion of buttress material (18/20) and excess cut-away pericardial tissue (104) which is discarded. The tissue is then placed upon a mounting device and packaged (90) prior to sterilization via e-beam (92).

If used wet, the now chemically fixed tissue is removed from the form. The tissue is then placed face down (support ring up) and circularly cut evenly about the support ring to the desired diameter. The diameter is dictated by outer diameter of desired intraluminal stapler. The tissue can then placed upon a mounting device if required. The tissue is treated with a solution of 70% ethanol, 1% propylene oxide for 48 to 432 hours. After the initial 70% ethanol, 1% propylene oxide treatment, tissue can be inspected and stored thereafter in jars filled with 70% ethanol, 1% propylene oxide for 75 hours minimally.

Thereafter the tissue is subjected to another quality inspection. The jarred tissue is drained and refilled with fresh 70% ethanol, 1% propylene oxide for 14 days minimally. After this step, a quality assurance sterility check is conducted during which the 70% ethanol, 1% propylene oxide is drained and the inspected tissue is immersed in sterile water containing 1% propylene oxide. Alternatively to this procedure, the tissue can be terminally sterilized with γ-irradiation, which decreases the required number of ethanol-containing solution changes. The caps are torqued in accordance with established procedures. A quality inspection is conducted. Finally, the package is labeled and the final inspection and release to stores is conducted (94).

EXAMPLES

Example #1

Roux-En-Y Gastric Bypass Procedure Using Circular Stapler Buttress Material

The surgical steps to create a Roux-en-Y gastric bypass using circular stapler buttress material are as follows. After the institution of general endotracheal anesthesia, a nasogastric tube and catheter are placed. Pneumatic sequential compression devices are applied to the lower extremities. The patient is given 2,500 units of low-molecular weight heparin and an intravenous dose of ampicillin/sulbactam. Trocars are then placed in the umbilicus and various ports. A "Y" connector is attached to the insufflator to allow for carbon dioxide insufflation through two trocars.

The stomach is approached through the gastrohepatic ligment and transected with a 45-mm endoscopic linear stapler such as those manufactured by Ethicon Endo-Surgery, (Cincinnati, Ohio), leaving a 15 to 20 cc gastric pouch. The patient is placed in steep Trendelenherg's position, and the greater omentum and transverse colon are reflected caudally. The jejunum is transected with an endoscopic stapler approximately 25 cm to 40 cm distal to the ligament of Trietz. The mesentery is split vertically with ultrasonic coagulating shears. The Roux (distal jejunum) limb is then passed to the esophageal hiatus.

Circular buttress material is applied to a circular stapler of any diameter. The anvil and cartridge of the circular stapler are separated. The circular buttress is then introduced to the anvil and the cartridge and is pressed into place so that the buttress lies flat against each stapler component "face". A viscous gel (e.g. a standard gel as available under the tradename "PSD" from Biovascular, Inc.) may be applied prior to positioning to enhance retention of the buttress on the stapler during manipulation in the body. Alternatively, a pressure-sensitive adhesive may be deposited on the buttress as a part of the manufacturing process in place of gel application by the end-user. The anvil buttress and cartridge buttress are then mated to the anvil and cartridge of the stapler, respectively. Following attachment of the buttress material, the anvil may be reattached to the cartridge and closed onto a foam support in order to enhance the adhesion between buttress and stapler. After an appropriate period of compression, the anvil is then opened, the anvil and foam support (if used) are removed, and the stapler is then ready to use.

For this procedure, a small (<25 mm) "flip top" circular stapler is used to allow for the safe, antegrade passage of the larger anvil through the esophagus. The flip top of the stapler anvil is flipped. A suture is passed between the top of the flipped anvil and the small hole in the tip of the anvil's post and tied. After the flip top is secured into the flipped position, the distal (larger) end of a nasogastric tube is transected just proximal to its air or sump port. The stapler's anvil will fit snugly into the lumen of the cut nasogastric tube at this point. A silk stitch is used to secure the anvil in the nasogastric tube by passing the needle and suture through one side of the tube, through the small hole in the anvil's post, and out the other side of the tube. The suture is then tied to itself to secure the anvil within the nasogastric tube.

The nasogastric tube and anvil are coated with a sterile water-soluble lubricant, and the proximal nasogastric tube is positioned into the gastric pouch. When the tip of the proximal nasogastric tube reaches the staple line of the gastric pouch, a 4-mm gastrotomy is made over the tip of the nasogastric tube with laparoscopic scissors, and the tube is pulled into the abdomen. The nasogastric tube is slowly advanced and pulled out through one of the lower abdominal trocars. As the tube is slowly pulled into the abdomen, the anvil is guided through the oropharynx under direct vision via a laryngoscope. Once in the esophagus, the stapler head of the anvil slides down easily into position in the gastric pouch. After the tip of the anvil has passed through the gastrotomy, the sutures holding the anvil in the nasogastric tube and flip top of the anvil are cut. The anvil is advanced until the flip top returns to its normal perpendicular position. To further facilitate removing the anvil from the nasogastric tube, the tube where the post is inserted is split with a harmonic scalpel. This instrument quickly cuts through the plastic, allowing the nasogastric tube to be pulled free and out to the abdomen. Alternatively, the anvil may be introduced into the gastric pouch laproscopically via a hole made in the pouch using a harmonic scalpel. This allows a larger stapler (>26 mm) to be used.

The staple line of the Roux jejunal limb is excised with the harmonic scalpel. The fastener head of the stapler is introduced directly through the abdominal wall. The stapler passed into the opening in the Roux jejunal limb and then several centimeters distally. The post of the anvil protruding through the gastric pouch is locked onto the fastener head. The anastomosis is stapled in the standard fashion by carefully positioning the tissue and firing the stapler. The positioning (i.e. discarded) portion(s) of the buttress are cut from the buttress portions after firing the stapler. This remnant material, as well as circular portions of the small bowel and pouch, are then removed from the patient along with the stapler. It is customary for the surgeon to inspect the condition of the tissue "rings" for integrity, as this is an indication of a circumferential anastomosis. At this point remnant buttress material can be discarded along with the used stapler.

The open end of the Roux limb is then closed with an endoscopic linear stapler. The Roux-en-Y enteroenterostomy is created 60 cm to 100 cm distal to the gastrojejunal anastomosis with an endoscopic linear stapler using standard laparoscopic anastomotic techniques. Prior to closing the trocar sites, the gastrojejunal anastomosis is tested with methylene blue infused through a nasogastric tube that will remain postoperatively.

Example #2

Creation of a Colorectal Anastomosis Using Circular Stapler Buttress Material

Circular staplers are also used in colorectal surgery to create a leak-proof anastamosis between large intestine and the rectum. This procedure can also be improved through the use of circular stapler buttress material. As in the previous example, buttress material is positioned on the anvil and cartridge components and pressed into place so that the buttress lies flat against each stapler "face". A viscous gel of the type described above may be applied prior to positioning to enhance retention of the buttress on the stapler during manipulation in the body. Alternatively, a pressure sensitive adhesive may be deposited on the buttress as a part of the manufacturing process in place of gel application by the end-user. Following attachment of the buttress material, the anvil is reattached to the cartridge and closed onto a foam support in order to enhance the adhesion between buttress and stapler. After an appropriate period of compression, the anvil is then opened, the anvil and foam support (if used) are removed, and the stapler is then ready to use.

In colorectal surgery, the distal fastener head is usually inserted through the anus. In most instances, the maneuver is facilitated using a Fansler or Chelsey-Eaton anoscope which allows gradual, controlled dilation of the anal sphincter muscles. After removal of the obturator, the stapler shaft can easily be passed through the anoscope. Once through the sphincter, the stapler must be inserted up to the resected end of the rectum. The anvil is positioned into the resected end of the large intestine. The shaft of the anvil extends beyond the end of the intestine with a purse-string suture holding tissue in place.

The anvil and cartridge of the stapler are connected and the stapler is closed and fired. Positioning (discarded) portions of the buttress are cut from the buttress upon firing of the stapler. This remnant material as well as circular portions of the large bowel and rectum are removed from the patient along with the stapler. The integrity of the anastomosis is then assessed as in Example #1.

What is claimed is:

1. A combination medical device comprising:
   a) a circular stapler instrument, comprising a staple cartridge component having a central recessed aperture and corresponding anvil component having a central recessed aperture, and
   b) one or more portions of buttress material adapted to be a) stably positioned upon the staple cartridge and/or anvil components of the stapler instrument prior to, or at the time of, use, b) while in position upon the stapler instrument component(s), to then be delivered to a tissue site in combination with the stapler instrument components, c) upon delivery of the components and positioned material portion(s) to the tissue site, to provide a first region of buttress material as a staple line buttress seal between joined tissue sections upon activation of the stapler instrument, and optionally, d) to permit the removal of one or more portions of a second region of the buttress material upon activation of a stapler instrument knife provided by the stapler instrument, wherein the buttress material portion adapted to fit the cartridge component comprises a circumferential disc having an integral raised center portion adapted to fit the central recessed aperture of the cartridge, and the buttress material portion adapted to fit the anvil component comprises a circumferential disc having an integral raised center portion adapted to fit the central recessed aperture of the anvil.

2. A combination according to claim 1 wherein the buttress material comprises preformed animal tissue.

3. A combination according to claim 2 wherein the preformed animal tissue comprises pericardium.

4. A combination according to claim 3 wherein the pericardium has been formed by a process that includes the steps of wrapping the pericardium onto a mandrel or other model shape, soaking the wrapped pericardium in a crosslinking solution, removing the pericardium from the mandrel or other model shape, and sterilizing the pericardium.

5. A combination according to claim 1 wherein the buttress material is provided as a plurality of portions, including one portion adapted to fit the staple cartridge and another portion adapted to fit the anvil component.

6. A combination according to claim 5 wherein the buttress material portions each comprise two or more regions, including a first region adapted to serve as the staple line buttress itself, together with a second region adapted to assist in positioning and/or retaining the buttress material upon a stapler instrument component.

7. A combination according to claim 6 wherein one or more portions of the second region are adapted to be removed from the tissue site upon formation of a staple seam and activation of a stapler instrument knife.

8. A combination according to claim 7 wherein the second region is generally concentric to, and integral with, the first region, providing a desired three dimensional and/or topographic structure adapted to position and/or retain the materials in place upon the respective stapler instrument component.

9. A combination according to claim 8 wherein the preformed animal tissue comprises pericardium that has been preformed by a process that includes the steps of wrapping the pericardium onto a mandrel or other model shape, soaking the wrapped pericardium in a crosslinking solution, removing the pericardium from the mandrel or other model shape, and sterilizing the pericardium.

10. A method of performing a surgical stapling procedure, the method comprising the steps of providing a combination according to claim 1, and employing the circular stapler instrument and the one or more portions of buttress material to provide a buttressed surgical seam between abutting tissue portions.

11. A method according to claim 10 wherein the buttress material comprises preformed animal tissue.

12. A method according to claim 11 wherein the preformed animal tissue comprises pericardium.

13. A method according to claim 12 wherein the pericardium has been formed by a process that includes the steps of wrapping the pericardium onto a mandrel or other model shape, soaking the wrapped pericardium in a crosslinking solution, removing the pericardium from the mandrel or other model shape, and sterilizing the pericardium.

14. A method according to claim 10 wherein the buttress material portions are provided as a plurality of portions, including one portion adapted to fit the staple cartridge and another portion adapted to fit the anvil component.

15. A method according to claim 14 wherein the buttress material portions each comprise two or more regions, including a first region adapted to serve as the staple line buttress itself, together with a second region adapted to assist in positioning and/or retaining the buttress material upon a stapler instrument component.

16. A method according to claim 15 wherein one or more portions of the second region are adapted to be removed from the tissue site upon formation of the staple seam and activation of a stapler instrument knife.

17. A method according to claim 16 wherein the second region is generally concentric to, and integral with, the first region, providing a desired three dimensional and/or topographic structure adapted to position and/or retain the materials in place upon the respective stapler instrument component.

18. A method according to claim 17 wherein the preformed animal tissue comprises pericardium that has been preformed by a process that includes the steps of wrapping the pericardium onto a mandrel or other model shape, soaking the wrapped pericardium in a crosslinking solution, removing the pericardium from the mandrel or other model shape, and sterilizing the pericardium.

19. A kit for use in a circular stapling procedure employing a circular stapler instrument that comprises a staple cartridge component having a central recessed aperture and a corresponding anvil component having a central recessed aperture, the kit comprising one or more generally circular portions of buttress material adapted to be a) stably positioned upon the staple cartridge and/or anvil components of the stapler instrument prior to, or at the time of, use, b) while in position upon the stapler component(s), to then be delivered to a tissue site in combination with the stapler components, c) upon delivery of the components and positioned material portion(s) to the tissue site, to provide a first region of buttress material as a staple line buttress seal between joined tissue sections upon activation of the stapler, and optionally, d) to permit the removal of one or more portions of the second region of the buttress material upon activation of a stapler knife provided by the stapler, wherein the buttress material portion adapted to fit the cartridge component comprises a circumferential disc having an integral raised center portion adapted to fit the central recessed aperture of the cartridge, and the buttress material portion adapted to fit the anvil component comprises a circumferential disc having an integral raised center portion adapted to fit the central recessed aperture of the anvil.

20. A kit according to claim 19 wherein the buttress material comprises preformed animal tissue.

21. A kit according to claim 20 wherein the preformed animal tissue comprises pericardium.

22. A kit according to claim 21 wherein the pericardium has been formed by a process that includes the steps of wrapping the pericardium onto a mandrel or other model shape, soaking the wrapped pericardium in a crosslinking solution, removing the pericardium from the mandrel or other model shape, and sterilizing the pericardium.

23. A kit according to claim 19 wherein the buttress material is provided as a plurality of buttress material portions, including one portion adapted to fit the staple cartridge and another portion adapted to fit the anvil component.

24. A kit according to claim 23 wherein the buttress material portions each comprise two or more regions, including a first region adapted to serve as the staple line buttress itself together with a second region adapted to assist in positioning and/or retaining the buttress material portion upon a stapler instrument component.

25. A kit according to claim 24 wherein one or more portions of the second region are adapted to be removed from the tissue site upon formation of a staple seam and activation of a stapler instrument knife.

26. A kit according to claim 25 wherein the second region is generally concentric to, and integral with, the first region, providing a desired three dimensional and/or topographic structure adapted to position and/or retain the materials in place upon the respective stapler instrument component.

27. A kit according to claim 26 wherein the preformed animal tissue comprises pericardium that has been preformed by a process that includes the steps of wrapping the pericardium onto a mandrel or other model shape, soaking the wrapped pericardium in a crosslinking solution, removing the pericardium from the mandrel or other model shape, and sterilizing the pericardium.

28. A method of forming a buttress material for use in a kit according to claim 19, the method comprising the steps of treating pericardium positioned upon a form of suitable size and shape to approximate that of a surgical stapler instrument component.

29. A method according to claim 28 wherein the buttress material comprises preformed animal tissue.

30. A method according to claim 29 wherein the preformed animal tissue comprises pericardium.

31. A method according to claim 30 wherein the pericardium has been formed by a process that includes the steps of wrapping the pericardium onto a mandrel or other model shape, soaking the wrapped pericardium in a crosslinking solution, removing the pericardium from the mandrel or other model shape, and sterilizing the pericardium.

32. A method according to claim 28 wherein the buttress material is provided as a plurality of portions, including one portion adapted to fit the staple cartridge and another portion adapted to fit the anvil component.

33. A method according to claim 32 wherein the buttress material portions each comprise two or more regions, including a first region adapted to serve as the staple line buttress itself, together with a second region adapted to assist in positioning and/or retaining the buttress material upon a stapler instrument component.

34. A method according to claim 33 wherein one or more portions of the second region are adapted to be removed from the tissue site upon formation of a staple seam and activation of a stapler instrument knife.

35. A method according to claim 34 wherein the second region is generally concentric to, and integral with, the first region, providing a desired three dimensional and/or topographic structure adapted to position and/or retain the materials in place upon the respective stapler instrument component.

36. A method according to claim 35 wherein the preformed animal tissue comprises pericardium that has been preformed by a process that includes the steps of wrapping the pericardium onto a mandrel or other model shape, soaking the wrapped pericardium in a crosslinking solution, removing the pericardium from the mandrel or other model shape, and sterilizing the pericardium.

37. A combination medical device comprising:
a) a circular stapler instrument, comprising a staple cartridge component and corresponding anvil component, and
b) one or more portions of buttress material adapted to be a) stably positioned upon the staple cartridge and/or anvil components of the stapler instrument prior to, or at the time of, use, b) while in position upon the stapler instrument component(s), to then be delivered to a tissue site in combination with the stapler instrument components, c) upon delivery of the components and positioned material portion(s) to the tissue site, to provide a first region of buttress material as a staple line buttress seal between joined tissue sections upon activation of the stapler instrument, and optionally, d) to permit the removal of one or more portions of a second region of the buttress material upon activation of a stapler instrument knife provided by the stapler instrument,
wherein at least one of the buttress material portions comprises two or more regions, including a first region adapted to serve as the staple line buttress itself, together with a second region adapted to assist in positioning and/or retaining the buttress material upon a stapler component, and wherein one or more portions of the second region are adapted to be removed from the tissue site upon formation of the staple seam and activation of a stapler knife, the second region being generally concentric to the first region, the first and second regions cooperating to provide a desired three dimensional and/or topographic structure adapted to position and/or retain the materials in place upon the respective stapler component.

38. A combination according to claim 37 wherein the first and second regions are adapted to be separated upon activation of a stapler knife, in a manner sufficient to permit the separated first region to provide a buttressed surgical seam between abutting tissue portions and to permit the separated second region to be removed from the tissue site.

39. A combination according to claim 37 wherein one or more portions of the second region are adapted to be removed from the tissue site upon formation of a staple seam and activation of a stapler instrument knife.

40. A combination according to claim 39 wherein the second region is generally concentric to, and integral with, the first region, providing a desired three dimensional and/or topographic structure adapted to position and/or retain the materials in place upon the respective stapler instrument component.

41. A method of performing a surgical stapling procedure, the method comprising the steps of providing a combination according to claim 37, and employing the circular stapler instrument and the one or more portions of buttress material to provide a buttressed surgical seam between abutting tissue portions,
wherein at least one of the buttress material portions comprises two or more regions, including a first region adapted to serve as the staple line buttress itself, together with a second region adapted to assist in positioning and/or retaining the buttress material upon a stapler component, and wherein one or more portions of the second region are adapted to be removed from the tissue site upon formation of the staple seam and activation of a stapler knife, the second region being generally concentric to the first region, the first and second regions cooperating to provide a desired three dimensional and/or topographic structure adapted to position and/or retain the materials in place upon the respective stapler component.

42. A method according to claim 41 wherein the first and second regions are adapted to be separated upon activation of a stapler knife, in a manner sufficient to permit the separated first region to provide a buttressed surgical seam between abutting tissue portions and to permit the separated second region to be removed from the tissue site.

43. A method according to claim 41 wherein one or more portions of the second region are adapted to be removed from the tissue site upon formation of a staple seam and activation of a stapler instrument knife.

44. A method according to claim 43 wherein the second region is generally concentric to, and integral with, the first region, providing a desired three dimensional and/or topographic structure adapted to position and/or retain the materials in place upon the respective stapler instrument component.

45. A kit for use in a circular stapling procedure employing a circular stapler instrument that comprises a staple cartridge component and a corresponding anvil component,
the kit comprising one or more generally circular portions of buttress material adapted to be a) stably positioned upon the staple cartridge and/or anvil components of the stapler instrument prior to, or at the time of, use, b) while in position upon the stapler instrument component(s), to then be delivered to a tissue site in combination with the stapler instrument components, c) upon delivery of the components and positioned material portion(s) to the tissue site, to provide a first region of buttress material as a staple line buttress seal between joined tissue sections upon activation of the stapler instrument, and optionally, d) to permit the removal of one or more portions of a second region of the buttress material upon activation of a stapler instrument knife provided by the stapler instrument, wherein at least one of the buttress material portions comprises two or more regions, including a first region adapted to serve as the staple line buttress itself together with a second region adapted to assist in positioning and/or retaining the buttress material upon a stapler component, and wherein one or more portions of the second region are adapted to be removed from the tissue site upon formation of the staple seam and activation of a stapler knife, the second region being generally concentric to the first region, the first and second regions cooperating to provide a desired three dimensional and/or topographic structure adapted to position and/or retain the materials in place upon the respective stapler component.

46. A kit according to claim 45 wherein the first and second regions are adapted to be separated upon activation of a stapler knife, in a manner sufficient to permit the separated first region to provide a buttressed surgical seam between abutting tissue portions and to permit the separated second region to be removed from the tissue site.

47. A kit according to claim 45 wherein one or more portions of the second region are adapted to be removed from the tissue site upon formation of a staple seam and activation of a stapler instrument knife.

48. A kit according to claim 47 wherein the second region is generally concentric to, and integral with, the first region, providing a desired three dimensional and/or topographic structure adapted to position and/or retain the materials in place upon the respective stapler instrument component.

49. A method of forming a buttress material for use in a kit according to claim 45, the method comprising the steps of treating pericardium positioned upon a form of suitable size and shape to approximate that of a surgical stapler instrument component, wherein at least one of the buttress material portions comprises two or more regions, including a first region adapted to serve as the staple line buttress itself, together with a second region adapted to assist in positioning and/or retaining the buttress material upon a stapler component, and wherein one or more portions of the second region are adapted to be removed from the tissue site upon formation of the staple seam and activation of a stapler knife, the second region being generally concentric to the first region, the first and second regions cooperating to provide a desired three dimensional and/or topographic structure adapted to position and/or retain the materials in place upon the respective stapler component.

50. A method according to claim 49 wherein the first and second regions are adapted to be separated upon activation of a stapler knife, in a manner sufficient to permit the separated first region to provide a buttressed surgical seam between abutting tissue portions and to permit the separated second region to be removed from the tissue site.

51. A method according to claim 49 wherein one or more portions of the second region are adapted to be removed from the tissue site upon formation of a staple seam and activation of a stapler instrument knife.

52. A method according to claim 51 wherein the second region is generally concentric to, and integral with, the first region, providing a desired three dimensional and/or topographic structure adapted to position and/or retain the materials in place upon the respective stapler instrument component.

53. A combination medical device comprising:
 a) a circular stapler instrument, comprising a staple cartridge and corresponding anvil component, either or both of which have a central recessed aperture, and
 b) one or more buttress materials adapted to be a) stably positioned upon the component(s) prior to, or at the time of, use, b) while in position upon the component(s), to then be delivered to a tissue site in combination with the component(s), c) upon delivery of the components and positioned material portion(s) to the tissue site, to provide a first region of buttress material as a staple line buttress seal between joined tissue sections upon activation of the stapler instrument, and optionally, d) to permit the removal of one or more portions of a second region of the buttress material upon activation of a stapler instrument knife provided by the stapler instrument,
 wherein one or more of the buttress materials comprises a circumferential disc having an integral raised center portion adapted to fit the central recessed aperture of the component(s).

54. A kit for use in a surgical stapling procedure employing a circular stapler instrument that comprises a staple cartridge and corresponding anvil component, either or both of which have a central recessed aperture, the kit comprising one or more buttress materials adapted to be a) stably positioned upon the component(s) prior to, or at the time of, use, b) while in position upon the component(s), to then be delivered to a tissue site in combination with the component(s), c) upon delivery of the components and positioned material portion(s) to the tissue site, to provide a first region of buttress material as a staple line buttress seal between joined tissue sections upon activation of the stapler instrument, and optionally, d) to permit the removal of one or more portions of a second region of the buttress material upon activation of a stapler instrument knife provided by the stapler instrument,
 wherein one or more of the buttress materials comprises a circumferential disc having an integral raised center portion adapted to fit the central recessed aperture of the component(s).

* * * * *